United States Patent [19]

Wijcik

[11] Plant 4,382

[45] Feb. 20, 1979

[54] DWARF McINTOSH APPLE TREE

[75] Inventor: Anthony C. Wijcik, Kelowna, Canada

[73] Assignee: Stark Brothers Nurseries & Orchards Company, Louisiana, Mo.

[21] Appl. No.: 890,867

[22] Filed: Mar. 24, 1978

[51] Int. Cl.[2] ..... A01H 5/03

[52] U.S. Cl. ..... Plt./34

[58] Field of Search ..... Plt./34

*Primary Examiner*—Robert E. Bagwill

*Attorney, Agent, or Firm*—Burns, Doane, Swecker & Mathis

[57] ABSTRACT

A new and distinct spur-type variety of McIntosh apple tree is provided which exhibits an extreme degree of dwarfness. The new variety was produced as a single limb mutation in a fifty year old standard McIntosh apple tree. The tree possesses an extremely compact, strong and rigid structure and bears fruit which is less intense in color than other spur-type McIntosh apple tree strains such as the Gatzke strain (non-patented), the Greenslade strain (U.S. Plant Pat. No. 2,982), and the Raikes strain (U.S. Plant Pat. No. 3,390).

2 Drawing Figures

SUMMARY OF THE INVENTION

The new variety was discovered by me in 1963 as a single limb sport growing in the top of a 50 year old standard McIntosh apple tree. The tree wherein the mutation occurred was growing in my orchard (Lot 4, Section 101, Township 26) at Kelowna, British Columbia, Canada. I was attracted to the new variety because of its distinctive compact and sturdy growing habit whereby large green leaves were borne on unusually closely spaced nodes, and the fruiting spurs were unusually closely spaced and numerous. This unique growing habit was quite different than that of other shoots on this standard bearing McIntosh apple tree. The characteristics of the new variety are also different than those of other spur-type McIntosh varieties.

It has been found that under the best of cultural conditions the annual terminal elongation of shoots seldom exceeds approximately 5 inches. Accompanying this reduction in terminal shoot elongation is a marked increase in shoot thickness, thereby giving the tree an extremely strong and rigid structure. The internodal spacing is compressed to such a degree that the new variety exhibits approximately twice as many nodes per linear foot than the McIntosh apple tree — Gatzke strain (non-patented). The fruit is typically McIntosh in flavor, but is inclined to be compressed in length, and on account of the heavier leaf cover is somewhat less well colored. The fruit is produced on shorter and heavier fruiting spurs which are more closely spaced and substantially more numerous per linear foot. The fruit also has a shorter pedicel and more flattened stem end and usually matures several days later than that of the regular McIntosh apple tree.

The new variety of apple tree possesses the following combination of characteristics: an extreme degree of dwarfness; limbs of unusual strength and rigidity; and when compared to the McIntosh apple tree — Gatzke strain (non-patented), the McIntosh apple tree — Greenslade strain (U.S. Plant Pat. No. 2,982) and the McIntosh apple tree — Raikes strain (U.S. Plant Pat. No. 3,390) possesses (a) a more upright growth habit, (b) thicker and greener leaves, (c) shorter and heavier fruiting spurs which are more closely spaced and more numerous per linear foot, (d) a shorter internodal spacing between leaves which is more heavily calipered, (e)

shoots of greater thickness, (f) a fruit color which is less intense, and (g) a fruit shape which is slightly more oblate with a shorter and thicker stem.

The Gatzke strain McIntosh apple tree referred to above is marketed by the Stark Bro's Nurseries and Orchards Company under the registered trademark "Starkspur".

Asexual propagation beginning in 1964 has demonstrated that the unique combination of characteristics of this new variety comes true to form and is established and transmitted through succeeding propagations.

BRIEF DESCRIPTION OF THE DRAWINGS

FIG. 1 shows in color as true as is reasonably possible a typical one year old shoot obtained during the Fall from the spur-type McIntosh apple tree — Gatzke strain wherein the internode length is illustrated. The leaves have been removed from the light green petioles so that the internodes are more readily apparent.

FIG. 2 shows in color as true as is reasonably possible a typical one year old shoot (left portion) extending from a two year old growth (right portion) obtained during the Fall from the McIntosh apple tree — Wijcik strain of the present invention wherein the shorter internode length is illustrated. The leaves have been removed from the light green petioles so that the internodes are more readily apparent. The apple of the new variety also is illustrated.

DETAILED DESCRIPTION OF THE DISCLOSURE

Figure 3:
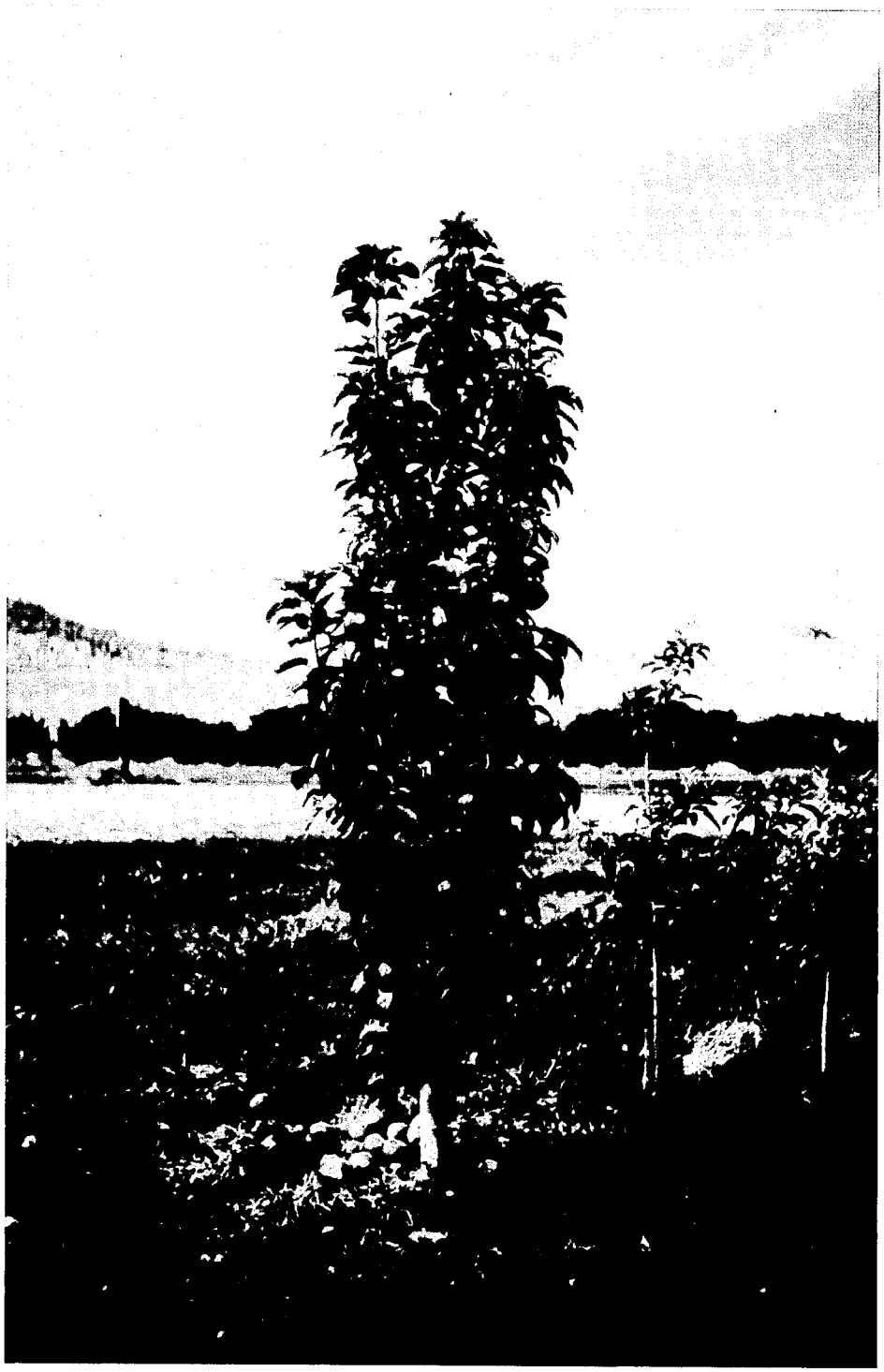
FIG. 3 shows the overall growth habit during the Fall of the McIntosh apple tree — Wijcik strain of the present invention (i.e. the larger tree). (The smaller trees in the photograph are to be disregarded.)

The following is a detailed description of my new variety with color terminology in accordance with the Nickerson Color Fan except where general color terms of ordinary dictionary color significance are obvious.

The specimens described were grown at Louisiana, Mo.

The first and last pickings were Sept. 1, 1977 and Sept. 10, 1977.

Tree: Small; upright; low-dense; vase-formed; slow growing; very hardy; productive; regular bearing.

*Trunk.*—Stocky; medium smooth.

*Branches.*—Thick; smooth; much branching; grey.

*Lenticels.*—Numerous; medium.

*Leaves.*—Length — about 3¾ inches; width — about 2-9/16 inches; large; medium wide; medium long; ovate; abruptly pointed; thick; Dark Green — Hue 2.5G 3/3; rugose.

*Margin.*—Coarsely serrate.

*Petiole.*—Length — about 1¼ inches; medium long; medium thick.

Flowers: Dates of first and full bloom — same as McIntosh apple tree — Gatzke strain; early; large; white.

Fruit: Medium firm — September 10.

*Size.*—Variable; axial diameter — about 2-9/16 inches; transverse — about 3⅛ inches; oblate — compressed transversely.

*Cavity.*—Symmetrical; flaring toward apex; acuminate; even; undulate; depth — about 7/16 inch; breadth — about 1¼ inches; markings, none.

*Basin.*—Symmetrical; rounded; pubescent; depth — about ½ inch; breadth — about 1½ inches; markings, none.

*Stem.*—Stout; pubescent; length — about ¼ inch.

*Calyx.*—Closed. Segments — Persistent; narrowly lanceolate; acute; length — about 3/16 inch; separated; ascending; converged from base. Outer surface — pubescent. Inner surface — pubescent.

*Eye.*—Small to non-existent.

*Skin.*—Thin; tough; glossy; waxed. Dots — obscure; many; small; submerged. Color of dots — whitish. Distribution of dots — fairly even. Ground color — greenish white to yellow. Color markings — blushed; bright. Color of markings — blushed. Bloom — moderate. Scarfskin — wanting. General color effect — Strong Red Hue 2.5R 4/10.

*Flesh.*—Rather juicy. Color of flesh — white. Texture — tender; fine; crisp. Flavor — sweet; delicate. Aroma — distinct. Quality — best.

*Core.*—Median. Bundle area (longitudinal section) — medium; broadly ovate; unsymmetrical at base; opposite; with cell. Halves of area — unequal; inconspicuous; in one whorl. Alternate bundle — approximate to distant — reaches tube at stamens. Core lines — meeting; in cross section indistinct; carpellary area distinct. Calyx-tube — glabrous toward base; apex broadly obconic; funnel form. Stem of funnel — short. Depth of tube to shoulder — about ¼ inch. Entire depth — about ½ inch. Styles — present; united. Stamens — two obscure; whorls; median. Auxillary cavity — wanting. Seed cells — open. Cell walls — distant; thick; tough. Length — about 11/16 inch. Breadth — about 7/16 inch. Longitudinal section — broadly oval; obtuse at apex. Surface — entire; smooth. Cross section — broad.

Seeds: Number perfect 4–6; number imperfect 0–2.

*Number in one cell.*—2.

*Length.*—About ¼ inch.

*Breadth.*—About 3/16 inch.

*Form.*—Acute.

*Color.*—Brown; dark.

Use: Multiple.

Keeping quality: Good.

*Number of days in ordinary storage.*—Same as all McIntosh.

Resistance to:

*Insects.*—Good.

*Diseases.*—Excellent. The fruit and foliage appear to be more tolerant to apple scab and powdery mildew than other McIntosh apple trees. Also, the trunk and roots are more tolerant to *Phytophthora cactorum* (crown rot) than standard McIntosh apple trees.

I claim:

1. A new and distinct variety of apple tree of the spur-type which is a mutation of a standard McIntosh apple tree substantially as shown and described, characterized by an extreme degree of dwarfness; limbs of unusual strength and rigidity; and when compared to the McIntosh apple tree — Gatzke strain (non-patented), the McIntosh apple tree — Greenslade strain (U.S. Plant Pat. No. 2,982) and the McIntosh apple tree — Raikes strain (U.S. Plant Pat. No. 3,390) possesses (a) a more upright growth habit, (b) thicker and greener leaves, (c) shorter and heavier fruiting spurs which are more closely spaced and more numerous per linear foot, (d) a shorter internodal spacing between leaves which is more heavily calipered, (e) shoots of greater thickness, (f) a fruit color which is less intense, and (g) a fruit shape which is slightly more oblate with a shorter and thicker stem.

* * * * *

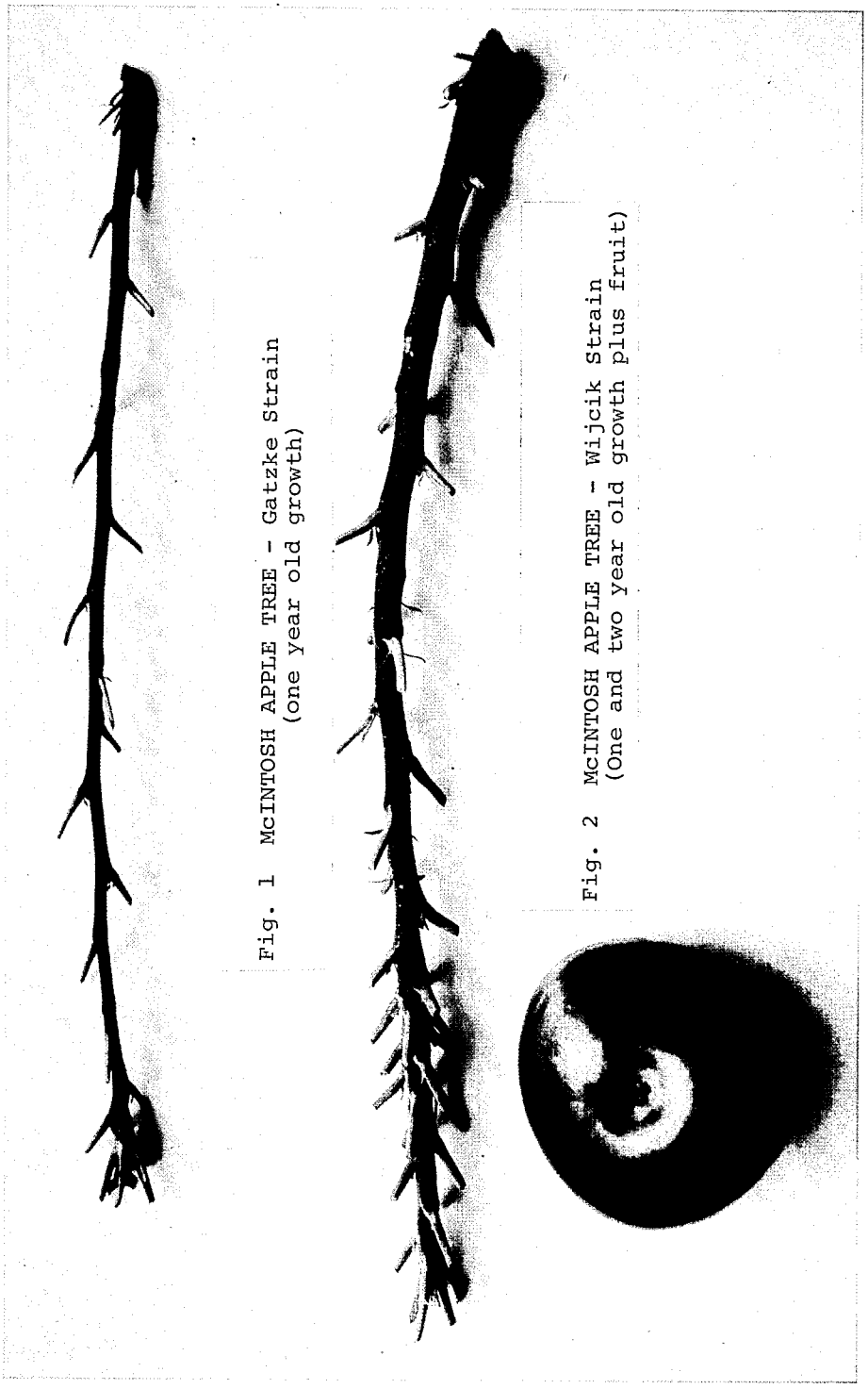
Fig. 1 McINTOSH APPLE TREE - Gatzke Strain (one year old growth)
Fig. 2 McINTOSH APPLE TREE - Wijcik Strain (One and two year old growth plus fruit)